(12) United States Patent
Johansson et al.

(10) Patent No.: US 6,290,827 B1
(45) Date of Patent: Sep. 18, 2001

(54) DEVICE FOR ELECTROCHEMICAL MEASUREMENT

(75) Inventors: Christer Johansson, Knivsta; Sten-Eric Lindquist, Uppsala, both of (SE)

(73) Assignee: CCL Connectors & Cables AB, Knivsta (SE)

( * ) Notice: Subject to any disclaimer, the term of this patent is extended or adjusted under 35 U.S.C. 154(b) by 0 days.

(21) Appl. No.: 09/674,807

(22) PCT Filed: Apr. 23, 1999

(86) PCT No.: PCT/SE99/00666
  § 371 Date: Nov. 6, 2000
  § 102(e) Date: Nov. 6, 2000

(87) PCT Pub. No.: WO99/57553
  PCT Pub. Date: Nov. 11, 1999

(30) Foreign Application Priority Data

May 6, 1998 (SE) .................................................. 9801584

(51) Int. Cl.[7] ...................................................... G01N 27/26
(52) U.S. Cl. .......................... 204/400; 204/286; 204/416; 204/212; 324/447; 324/450
(58) Field of Search ................................... 204/406, 400, 204/404, 416, 403, 434, 435, 286, 297 R, 212, 199, 200, 201, 213–218; 324/446–450

(56) References Cited

U.S. PATENT DOCUMENTS

4,889,608 12/1989 Eickmann ............................ 204/212

Primary Examiner—T. Tung
Assistant Examiner—Alex Noguerola
(74) Attorney, Agent, or Firm—Young & Thompson (57) ABSTRACT

A measuring system with a measuring body (2) mounted on a rotatable shaft (1) and being provided with electrodes (16) for measuring electrical currents obtained through chemical reactions within an analyte solution. In the rotatable shaft is housed an electronic unit (14) for converting the electric current to a measuring signal which is, via a transferring means (6), transferred in an analogue or digital representation to a measuring signal registrating means placed outside of the rotatable shaft.

10 Claims, 5 Drawing Sheets

DEVICE FOR ELECTROCHEMICAL MEASUREMENT

TECHNICAL FIELD OF THE INVENTION

The present invention relates to a measuring device for electrochemical determination of one or several chemical substances in a solution, and more specifically to a measuring device provided with a rotatable measuring body that is immersed in an electrolytic solution.

TECHNICAL BACKGROUND

A conventional amperometric determination of chemical components (hereinafter referred to as "analytes") in a solution is performed by immersing a number of electrodes, typically three, in the analyte solution. During electrochemical measurements an electrolyte, such as an ion forming salt or any other ion forming compound which when dissolved increases the conductivity of the solution, is usually added to the analyte solution. The three electrodes are referred to as working electrode (WE), reference electrode (RE) and counter electrode (CE). At least one working electrode is required, but there is no restriction to the use of any number of additional working electrodes, if this is advantageous in a specific desired type of measurement.

At least one working electrode is required, but there is no restriction to the use of any number of additional working electrodes, if this is advantageous for a specific desired type of measurement.

The reference electrode is designed to maintain a constant and well-defined electrical potential. With respect to this potential a fixed electrical potential, negative or positive, is applied on the working electrode by means of an external electronic device, a potentiostat. If analytes in the electrolyte solution being exposed to this potential undergoes reaction at the working electrode, an electrical current will flow between the working electrode and the counter electrode. This current may be measured, and reflects the concentration of the analyte(s) in the solution, while the direction of the measured current flow depends on whether an oxidation or a reduction process is present at the working electrode.

Ideally, no current flows through the reference electrode of a triple electrode system as described above. In the simplest case, the current measured between the working electrode and the counter electrode is directly proportional to the analyte concentration. The chemical reactions occurring at the counter electrode are usually of no interest from a measuring point of view. Therefore, the counter electrode is often separated from the analyte solution and is placed in a separate receptacle in a liquid being electrically connected with the analyte solution via a porous sintered glass filter.

Under certain conditions the reference electrode and the counter electrode may be combined. This is possible when the processes occurring at the counter electrode are reversible with regard to a component in the electrolyte, so that the rate of the electrochemical processes at the combined electrode is not current limiting for measuring an analyte at the working electrode.

A difficulty experienced during amperometric measurements is to achieve well-defined conditions in the solution at the boundary layer adjacent to the working electrode. Such well-defined conditions are of importance for obtaining reliable measurement results from which valid conclusions, such as determination of concentration, may be drawn. The rate at which processes occur at the working electrodes is regulated by the rate of electron transfer across the boundary layer between the analyte in the solution and the electrode, and/or by the rate of analyte transport through the solution to this boundary layer.

In order to achieve a well-defined transport of analyte towards the electrode the working electrode is rotated. Therefore, this is usually formed as a cylindrical body provided with one or several electrodes, usually working electrodes. In a typical embodiment, a central disk-shaped disk electrode and outside this an annular ring electrode, are positioned on the flat end surface whereby both these electrodes are working electrodes. Such a configuration is called a rotating ring-disk electrode.

In addition to working electrodes, reference and counter electrodes could be integrated in the rotating body as well. The present invention is concerned with a measuring device wherein the reference as well as the counter electrode is built into the rotating body, and in its simplest embodiment these are combined to one electrode, herein called RE/CE, under the provision of the situation described above with reversibly working RE/CE. In the borderline case of very low currents through RE/CE such a situation can always be created independently of whether the processes at RE/CE are ideally reversible, or not. In that case, the RE/CE potential is not altered which is the criterion for a good reference electrode. At the same time, currents from the working electrode are taken care of, which is the function of a counter electrode.

Therefore, the measuring conditions that are present in a conventional potentiostat controlled triple electrode system having separate electrodes WE, RE and CE could be achieved with good approximation, so that a double electrode system will be useful in practice for analyzing the content of components in an electrolyte.

A common type of conventional measuring device, for measurements of the type described above, is provided with a rotating electrode fixture on an elongated, hollow shaft. Connection leads extends through the shaft from the electrode surfaces. In their other ends, the connection leads are connected to a collector transferring device, i.e. electrically conducting areas are provided directly on the rotating shaft or as circumferential radial stripes or rings, whereby one such ring is being provided for each electrode, and each ring is being connected to the electrode via a lead, and for each ring a collecting shoe is fixedly mounted with respect to the environment and is connected to a potentiostat.

The U.S. Pat. No. 4,889,608 to G. Eickmann describes an electrode system of the type described above and for the case of one electrode, wherein the electrode is placed in a replaceable electrode fixture, which electrode fixture is mounted on an elongated solid metal shaft via an adaptor, the shaft also acting as an electric conductor. Also with this device electrical voltage and current are transferred to and from the electrode surface via a collector device to an electronic unit for registration of the measured signals.

However, conventional measuring devices of the type related above exhibit disadvantages that reduce their measuring performance.

The currents to be measured are often very small, especially when the analyte concentration is low or when inactive electrochemical processes are studied. However, collector couplings are characteristic in that they tend to generate interferences that are superimposed onto the measuring signal, and at the low analyte currents to be measured these interferences have a perceivable negative influence on the measuring precision.

The subsequent amplification of the measuring signal is of limited value since also the interference is amplified to a corresponding extent.

SUMMARY OF THE INVENTION

The present invention, as defined in claim 1, relates to a system for electrochemical measurements, such as concentration determination analysis, wherein all electrodes utilized in the system (one or several working electrodes, reference electrode, counter electrode) directly or via an adaptor are disposed on a rotatable shaft, and in particular to such a system wherein the reference electrode and the counter electrode are combined to one electrode, RE/CE.

It is an object of the invention to provide a design of such a measuring system exhibiting improved signal to noise ratio when measuring analyte solutions.

To achieve this object, the present invention provides a measuring system wherein the rotatable shaft that directly or via an electrode fixture holds the electrodes also houses an electronic unit, said electronic unit being operative to process signals received from the electrodes before they are transferred to the environment. As the signal processing, such as signal amplification, is made before the signals are transferred to the environment, the signals are processed in a state substantially without interferences. If interference is superimposed at a later stage, for example when the processed signal is transferred to the environment via a collector, the influence of interference on the signal is less than in a corresponding case with a conventional measuring equipment. By forming the shaft of a metal, it is possible to shield the electronic unit from electromagnetic radiation.

BRIEF DESCRIPTION OF THE DRAWINGS

Illustrative embodiments of the invention described in general terms above are described in more detail below, with the embodiments illustrated in the attached drawings wherein.

DETAILED DESCRIPTION OF EMBODIMENTS

Figure 1:
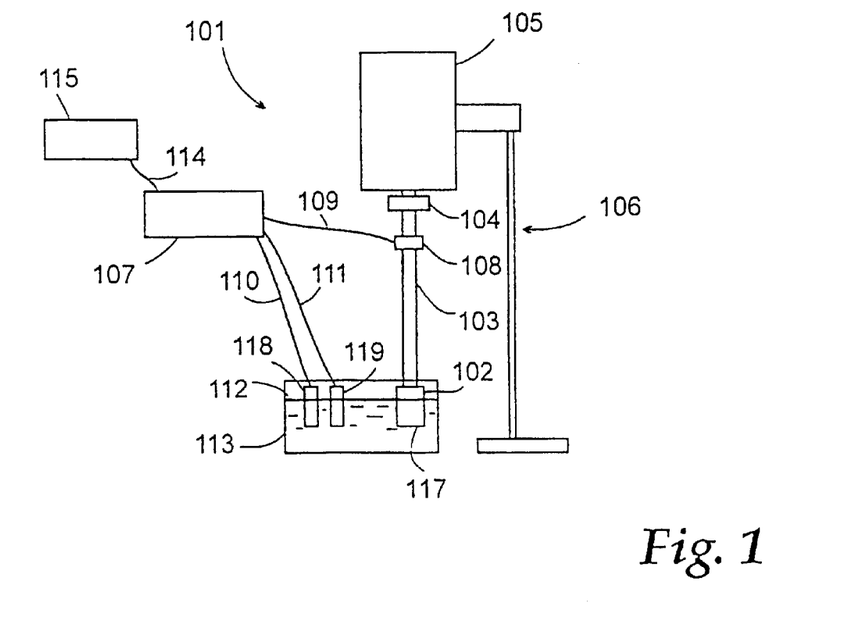
FIG. 1 is a schematical elevation view of a conventional measuring system.

First, a typical conventional measuring system shall be described, in general terms, as a background connection with reference to the schematical illustration of FIG. 1. A typical conventional measuring system 101 includes a measuring body 102 attached to a shaft 103. The shaft is, in its turn, connected to a motor 105 via a coupling device 104, in order to make the measuring body and the shaft rotatable. The motor is mounted onto a stand 106.

On the bottom surface 102 of the measuring body is disposed at least one working electrode 117. This working electrode is electrically connected to a potentiostat 107 via a lead (not shown) running through the shaft 103, a conventional collector coupling 108 and a cable 109. A reference electrode 118 and a counter electrode 119 are connected to the potentiostat via the cables 110 and 111, respectively.

In use, the electrodes 117, 118 and 119 (the working electrode 117 being rotated) are immersed in an electrolyte and analyte solution 112 in a vessel 113. By providing a voltage across the working electrode a current is generated at the working electrode and is transferred to the potentiostat via the collector coupling 108. The potentiostat outputs a measuring signal 114 based on the received current signal to a registering means 115. As the current signal crosses the collector coupling it receives interfering noise from the collector coupling, and this interference noise is also present in the measuring signal delivered from the potentiostat.

Cables connecting to a power source have been omitted in FIG. 1 for reasons of clarity.

Figure 2:
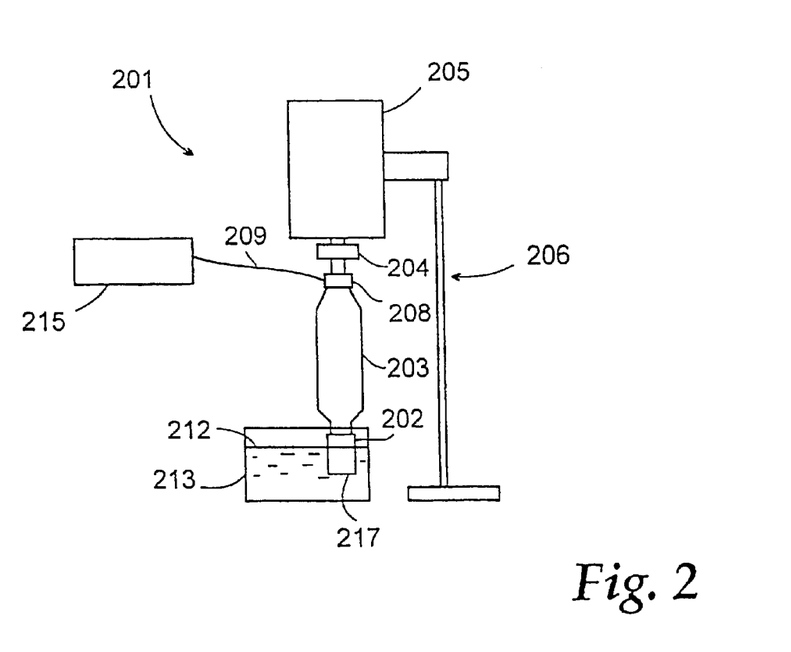
FIG. 2 is a schematical elevation view of an embodiment of a measuring system according to the present invention.

FIG. 2 illustrates schematically an embodiment of a measuring system 201 according to the present invention. The measuring system 201 comprises a measuring body 202 attached to a shaft 203, wherein the shaft 203 is hollow and houses an electronic unit (not shown in FIG. 2). The shaft, in its turn, is connected to a motor 205 via a coupling device 204, in order to make the measuring body and the shaft rotatable. The motor is mounted onto a stand 206. The coupling device may, as in the embodiment of the illustration, for example be a screw joint provided directly on the motor shaft or a power transmission such as a gear reduction, belt transmission or similar.

All electrodes 217 necessary for the system are provided on the bottom surface 202 of the measuring body, including at least one working electrode and a combined reference and counter electrode. The electrodes are connected to the electronic unit via leads (not shown) extending through the shaft 203. The electronic unit processes the signals from the electrodes to provide an output measuring signal that is transferred to a registering means 215 via a transferring means 208.

In one embodiment, for example, the transferring means consists of a conventional collector coupling and will then require a signal transmission cable 209 to the registering means 215. In a specific embodiment, as described below, the transferring means consists of a means for wireless transmission of the measuring signal information, in which case the signal path designated at 209 should be interpreted as a path of radiation.

In use, the measuring body 202 with its electrodes 217 is immersed in an electrolyte and analyte solution 212 in a vessel 213, and the measuring body is being rotated. By providing a voltage across the electrodes a current signal is generated at the working electrode and is transferred to the electronic unit where it is processed to be transferred, in a later step, to the registering means 215, such as a computer or a signal recording equipment, via the transferring means 208.

Figure 3:
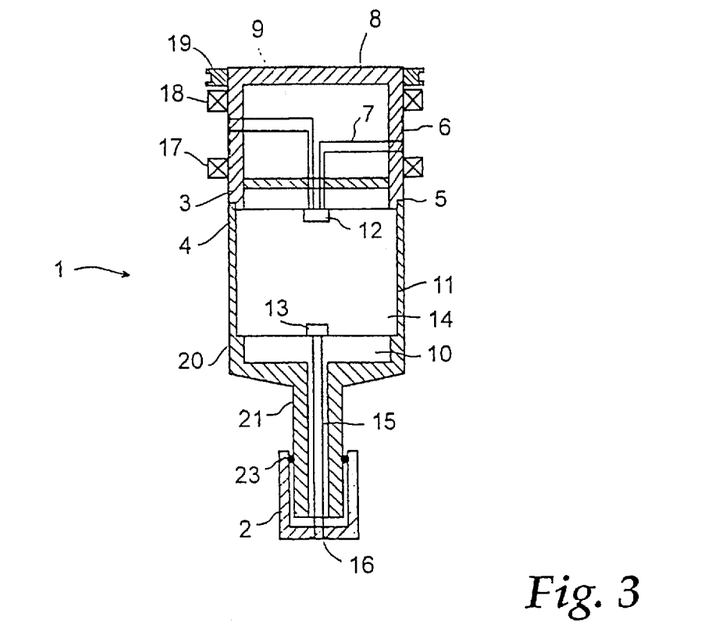
FIG. 3 is a schematical cross sectional view of an embodiment of a rotating shaft and a measuring body of a measuring system according to the present invention.

FIG. 3 is a schematical view of an embodiment of a rotatable shaft 1, with an attached measuring body 2, for use in a measuring equipment according to the present invention.

The rotatable shaft comprises an upper 3 and a lower 4 shaft section, both being hollow and attachable to each other with, for example, a thread 5. The shaft sections are formed of any material being suitable for the environment in which the measuring equipment is to be used, but it is preferred to form them of an electromagnetically shielding material, such as aluminum, to be effective to shield the interior from transmitted or received interference. The shaft sections could, at choice, be coated at the outside with a suitable corrosion preventing material such as polytetrafluoro ethylene, PTFE.

The upper hollow shaft section 3, that is of a substantially cylindrical shape and is closed at its upper end 8, comprises collector surfaces 6 (four in the embodiment shown) extending like stripes around the shaft section and being electrically insulated (not shown) with respect to thereto. Each collector surface is connected to an output lead 7 via an opening in the upper shaft section, i.e. there is one collector surface for each output lead (that is, four in the embodiment shown). The output leads extends through the hollow central part 9 of the upper shaft section.

The lower hollow shaft section 4 has an upper portion 20 connecting to a bottom portion 21 via a tapered intermediate portion. The upper portion 20 comprises an electronics compartment 10 in which an electronic unit 14, such as a circuit board, is disposed and held in place by slots 11 in the inner wall of the shaft section. The length and position of the slots are selected to ensure that the circuit board is clamped fixed when the upper shaft section 3 is threaded onto the lower shaft section.

The electronic unit 14 is provided with an output terminal 12 connecting the circuit board with the output leads 7 and also an input terminal 13 connected to electrodes 16 of the measuring body 2 bottom surface via input leads 15 (two being shown with the present embodiment). The input leads extend through the central part 22 of the bottom portion 21.

The rotating shaft 1 is suspended on a stand (not shown) via two ball bearings 17, 18. The stand is also equipped with a motor (not shown) for driving the rotation of the shaft 1. Preferably, the motor is coupled for direct drive of the shaft. Alternatively, the rotating movement is transferred via a power transferring means, such as a belt (not shown) coupled to a pulley 19 mounted on the shaft. Also, those components of the collector coupling that are not moving with the rotating shaft are not shown in FIG. 3.

The measuring body 2 is manufactured from a material with suitable mechanical and chemical properties, such as polyamide, PA. The measuring body may be formed as a component fixedly mounted onto the rotating shaft 1, but preferably it is formed as a replaceable component being optimized for the measurement at hand. The measuring body shown in FIG. 3 is a schematical example of an embodiment of a replaceable measuring body having a working electrode and a combined reference and counter electrode, wherein the measuring body is held in place on the lower portion 21 by the clamping force of a O-ring 23, said O-ring also having a sealing function. Other fastening means, such as threads or bayonet-mount may be used as well to detachably attach the measuring body to the rotating shaft. Preferably, the electrodes are arranged as conventional ring-disk electrodes.

Figure 4:
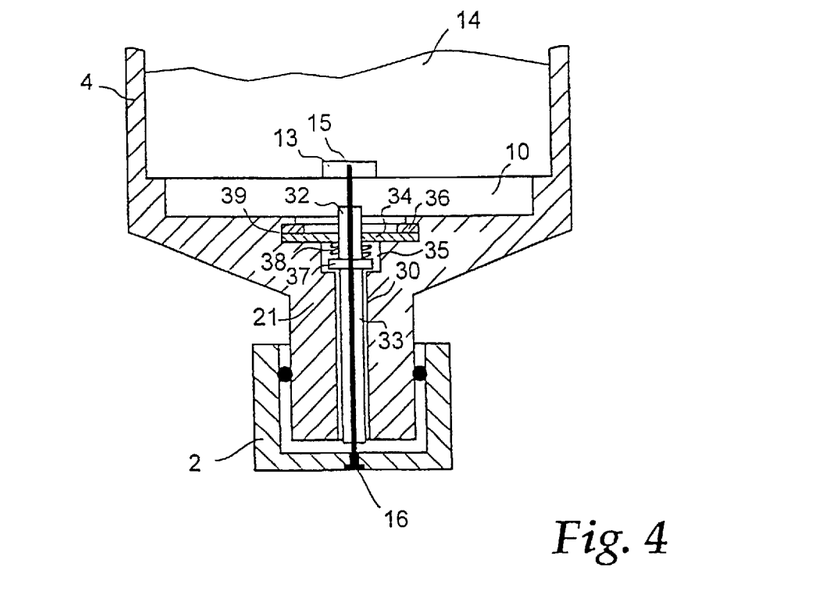
FIG. 4 is a schematical cross sectional view of an embodiment of the connection of an electrode to the electronic unit of a measuring system according to the present invention.

The input leads 15 are urged against the contact surfaces of the electrodes 16. The electrodes runs from the contact surfaces through the bottom part of the measuring body 2 and ends in measuring surfaces on the bottom plane surface of the measuring body. FIG. 4 shows in detail an embodiment of a connection between the electronic unit 14 and the electrodes 16, wherein parts corresponding to like parts in FIG. 3 have the same referral numbers. It should be noted that, for reasons of clarity, FIG. 4 only shows connection of one electrode to the electronic unit via a lead and for the same reason the length of the lead has consciously been shown disproportionally short, although usually more than one lead is disposed on the measuring body. Thus, it should be understood that a connection according to the figure shown should be made for each lead to its respective electrode.

As can be seen in FIG. 4, the circuit board of the electronic unit is connected to the electrode 16 of the measuring body 2 through a lead 15 detachably fitted into an input terminal 13, for instance a female plug of a conventional type. The lead extends through an axial bore 30, essentially in parallel with the central axis of the bottom portion 21 of the lower shaft section 4. A shrinking tubing, partitioned into an upper portion 32 and a lower portion 33, is shrunk onto the lead and serves as insulation with respect to the bottom shaft section but also as stiffening means. The upper end if the lead, thus stiffened, extends with a clearance through a hole in a washer 34 provided in a groove 39 in a centrally disposed recess 35 in the bottom of the electronic compartment 10. The washer is made of a stiff, electrically insulating material, such as polyamide, PA. The washer is locked in the groove with a conventional locking ring 36.

Below the washer 34, but above the bottom of the recess 35, is the upper shrinking tubing 32 separated from the lower shrinking tubing 33, and a sleeve 37 is fitted therebetween. The sleeve has a wider diameter than the shrinking tubing, to allow an end of a spring 38 to abut against the upper sleeve end while the other end of the spring abuts against the washer 34. Thus, the compression spring will bias the lead 15 such that the lead always press against the electrode 16 of the measuring body 2, thereby ensuring a proper electrical contact.

The connection of the output leads 7, according to FIG. 3, to the electronic unit 14 and the collector device, respectively, can be made in an entirely conventional way, such as using insertion plugs on the circuit board and solding to a collector ring. Similarly, the collector device is in itself of a conventional design and only needs to be adapted to suit the measures of the rotating shaft 1.

When using the measuring equipment, the measuring body 2 is immersed in the analyte solution to be analyzed. The shaft 1, and consequently the measuring body, is rotated by the motor via the pulley 17 in a way similar to the use of conventional measuring equipment.

The electronic unit 14 is provided with supply voltage via the collector coupling 6 in the upper shaft section 3 and, depending on the embodiment of the electronic unit, a reference voltage. The electronic unit provides an essentially constant voltage across the measuring electrodes via the input leads 15 and receives the current that, as a consequence, is generated between the electrodes 16 due to reactions in the analyte solution at the electrode surfaces.

Figure 5:
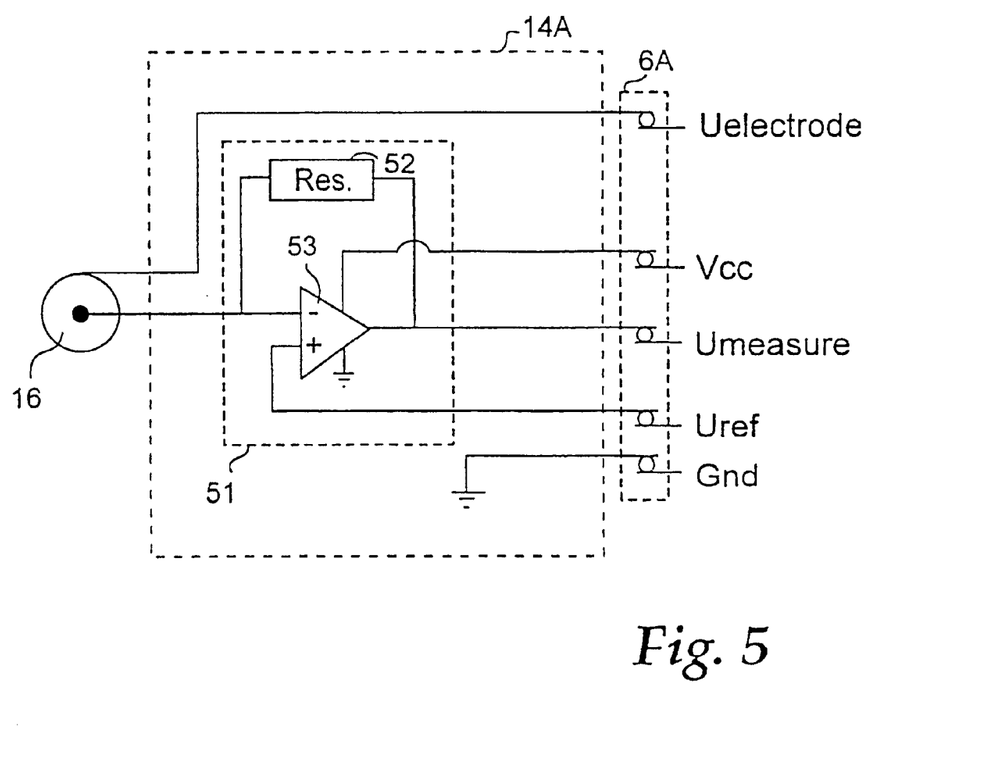
FIG. 5 is a block diagram of an embodiment of a signal processing circuit for use in a measuring equipment according to the present invention.

In a first embodiment of the electronic unit 14A, as shown in the diagram of FIG. 5, the measured current signal is amplified via a current/voltage converter 51A, consisting of a measuring range defining resistance 52 and an operational amplifier 53. The measured current is generated in the ring-disk electrode 16 being fed by an external voltage potential Uelectrode through a collector coupling 6A. Through the collector coupling is also a supply voltage Vcc provided to the operational amplifier, a reference voltage Uref and ground connection Gnd. The measuring signal, in the form of an analogue voltage Umeasure is transferred via the collector coupling to a suitable registering means (not shown).

Thus, the interferences from the collector coupling being superimposed on the measuring signal are smaller compared to the measuring signal than is the case with a conventional measuring equipment of a corresponding type, since they are superimposed on an already amplified signal. Therefore, the measuring signal exhibits a better signal-to-noise ratio.

Furthermore, since both the leads and the electronic unit are electromagnetically shielded from the surrounding environment by a suitable selection of the material of the rotating shaft, additional protection against external interference is achieved.

Figure 6:
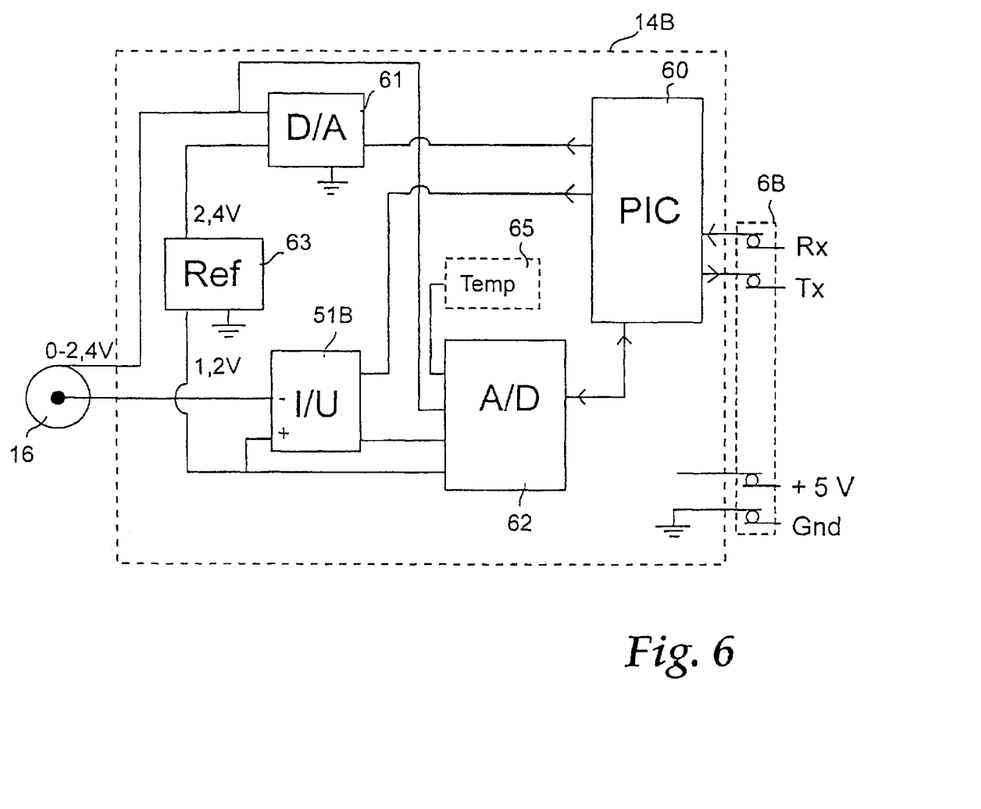
FIG. 6 is a block diagram of a second embodiment of a signal processing circuit for use in a measuring equipment according to the present invention.

A second, preferred embodiment of the electronic unit 14B, as illustrated by the diagram of FIG. 6, differs from the embodiment described above in that it in addition comprises an analogue/digital-converter to convert the measuring signal to a digital representation, and in that the reference voltages are generated internally in the electronic circuit. The digital measured information is delivered to the external environment via the collector coupling 6B.

As is generally shown in FIG. 6B, the electronic unit 14B is provided with a supply voltage +5V and a ground connection Gnd via the collector coupling 6B. The separate components and modules of the electronic unit are in themselves conventional and will therefore not be described in detail. A microprocessor 60 of PIC type (Periferal Interface Control) receives control signals Rx via the collector coupling. The microprocessor controls a digital/analogue converter 61 and a current/voltage converter 51B, as well as an analogue/digital converter 62. A reference voltage generator 63 converts the supply voltage of the electronic unit to two reference voltages (1.2 and 2.4 V, respectively) which are delivered to the current/voltage converter and the analogue/digital converter and digital/analogue converter, respectively.

The digital/analogue converter 61 delivers analogue supply voltage to the ring-disk electrode 16. Thereby, measuring current is generated and fed to the current/voltage converter 51B and after amplification the signal is delivered to the analogue/digital converter 62, whereto also an analogue voltage signal is delivered from the digital/analogue converter. Being controlled by the microprocessor 60, the analogue/digital converter delivers a digital representation of the measured signal to the microprocessor, which in its turn delivers the measuring information Tx to a selected registering means (not shown) via the collector coupling 6B.

Optionally (and therefore shown dashed), a temperature sensing module 65 may be included in the electronic unit 14B to obtain improved measuring accuracy, in a case where the measurement is temperature sensitive.

This second embodiment of the electronic unit 14B is advantageous, as compared to the first embodiment 14A, in that it allows for even higher signal-to-noise ratio since a digital signal in general is less sensitive to interference than is an analogue signal.

Furthermore, anyone skilled in the art realizes that even if it is not shown in a specific embodiment of this description, further modules may be added to the electronic unit to process the measuring information in any selected way before it is delivered to the environment.

Figure 7:
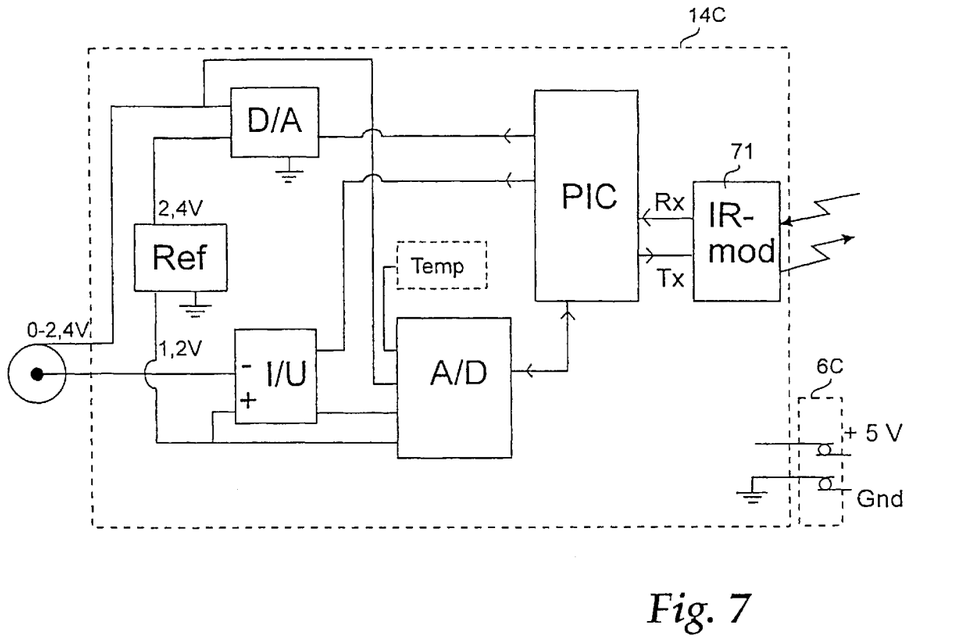
FIG. 7 is a block diagram of a third embodiment of a signal processing circuit for use in a measuring equipment according to the present invention.

A third embodiment of an electronic unit 14C, as illustrated in FIG. 7, differs from the second embodiment 14B shown in FIG. 6 in that it in addition comprises a module 71 for wireless transmission (in the embodiment shown represented with infrared radiation) of the digital signal to the environment surrounding the rotating shaft, and in that it also receives control signals from the environment. Of course, the information could be transferred by electromagnetic radiation of other frequencies than infrared frequencies. As the other components and modules of the electronic unit 14C corresponds to the similar parts of the second embodiment of an electronic unit 14B, the description thereof will not be repeated herein.

Thus, in the third embodiment the collector coupling 6C is used only to provide supply voltage(s) to the electronic unit 14C and reference voltages, if any. However, it should be noted that with this embodiment, as well as with other embodiments, it is possible to use a battery, inserted in the rotating shaft, as a power source.

A measuring equipment according to this third embodiment is disadvantageous in that its cost is higher than the previous embodiments, and requires a specifically arranged receiving equipment to register the output measuring information. However, the third embodiment provides the possibility to transfer measuring information to the environment substantially without any interference, and a higher degree of freedom for the placing of the measuring information registration equipment with respect to the measuring equipment is obtained.

Thus, with the present invention is provided a measuring equipment for electrochemical measuring of analyte solutions exhibiting improved signal-to-noise ratio as compared to conventional prior art equipment of a corresponding type.

The present invention has been described for the case of potentiostatic measurements, i.e. measurements wherein a constant voltage is applied across the reference electrode and electrical currents obtained in the analyte solution are measured. It is obvious for anyone skilled in the art that the invention is just as applicable for the case of galvanostatic measurement, wherein instead a constant current is provided and voltages obtained are registered.

What is claimed is:

1. A measuring device for electrochemical measurements in an analyte solution comprising: a rotatable shaft supported in a first end and driven for rotation by a drive means; a measuring body supported in a free, second end of the shaft; at least one electrode arranged on the measuring body for immersion in the analyte solution and generating a measuring signal in response to electrochemical reactions occurring in the analyte solution, said shaft incorporating an electronic unit housed in the shaft for processing the measuring signal, said electronic unit being provided signal transfer means arranged for feeding the processed signal to external equipment.

2. The measuring device of claim 1, wherein said processing of the signal refers to an amplification of the signal, before the signal is transferred to external equipment.

3. The measuring device of claim 1, wherein the signal generated by said at least one electrode is processed in said electronic unit and converted to measuring information of digital representation through an analogue/digital converter, incorporated in the electronic unit, before the signal is transferred to external equipment.

4. The measuring device of claim 1, wherein an electromagnetic radiation transmitting means is incorporated in the electronic unit and adapted for wireless transfer of the processed measuring signal to an external registering equipment.

5. The measuring device of claim 4, wherein said electromagnetic radiation transmitting means is a transmitter of infrared electromagnetic radiation.

6. A measuring device for electrochemical measurements in an analyte solution comprising: a rotatable shaft supported in a first end and driven for rotation by a drive means;

a measuring body supported in a free, second end of the shaft; at least one electrode arranged on the measuring body for immersion in the analyte solution and generating a measuring signal in response to electrochemical reactions occurring in the analyte solution, said shaft incorporating an electronic unit housed in the shaft for processing the measuring signal, said electronic unit being connected to signal transfer means arranged on the shaft for feeding the processed signal to external equipment, and     said shaft having an upper section and a lower section, and a hollow space formed therein for accommodating said electronic unit in clamping fixation as the sections are mutually connected.

7. The measuring device of claim 6, wherein the shaft is arranged for frictionally clamping a replaceable measuring body concentrically about the free end of the shaft.

8. The measuring device of claim 6, wherein the shaft is manufactured from an electromagnetically shielding material.

9. A measuring device for electrochemical measurements in an analyte solution comprising: a rotatable shaft supported in a first end and driven for rotation by a drive means; a measuring body supported in a free, second end of the shaft; at least one electrode arranged on the measuring body for immersion in the analyte solution and generating a measuring signal in response to electrochemical reactions occurring in the analyte solution, said shaft incorporating an electronic unit housed in the shaft for processing the measuring signal, said electronic unit being connected to signal transfer means arranged on the shaft for feeding the processed signal to external equipment, and     said measuring body being replaceable and having the shape of a tubular sleeve, concentrically attached about the free end of the shaft, the sleeve having a bottom plane carrying said at least one electrode extended through the bottom plane, such that one external end of each electrode is exposed to the analyte solution and an internal end of same electrode is electrically connected to the electronic unit housed in the shaft.

10. The measuring device of claim 9, wherein said at least one electrode of the measuring body is electrically connected to the electronic unit through a conductor that is accommodated in the free shaft end, electrically isolated from the shaft and spring biased in order to exert a resilient pressure towards the electrode in the attached position of the measuring body.

* * * * *